(12) United States Patent
Yasui et al.

(10) Patent No.: US 6,672,142 B2
(45) Date of Patent: Jan. 6, 2004

(54) METHOD AND APPARATUS FOR EVALUATING RETENTION TIME OF FOAM OF BEER

(75) Inventors: Kazuhisa Yasui, Yaizu (JP); Hiroshi Nakayama, Kawaguchi (JP)

(73) Assignee: Sapporo Breweries Ltd., Tokyo (JP)

( * ) Notice: Subject to any disclaimer, the term of this patent is extended or adjusted under 35 U.S.C. 154(b) by 19 days.

(21) Appl. No.: 10/158,139

(22) Filed: May 31, 2002

(65) Prior Publication Data

US 2002/0139176 A1 Oct. 3, 2002

Related U.S. Application Data

(63) Continuation of application No. 09/355,922, filed as application No. PCT/JP98/05581 on Dec. 10, 1998.

(30) Foreign Application Priority Data

Dec. 10, 1997 (JP) .............................. 9/340198

(51) Int. Cl.$^7$ .............................................. G01N 37/00
(52) U.S. Cl. ................................................... 73/60.11
(58) Field of Search .................. 73/60.11; 250/223 B

(56) References Cited

U.S. PATENT DOCUMENTS

| | | | | |
|---|---|---|---|---|
| 3,669,000 A | * | 6/1972 | Segel et al. | 426/592 |
| 4,610,888 A | * | 9/1986 | Teng et al. | 426/569 |
| 4,621,521 A | * | 11/1986 | Lattek et al. | 73/60.11 |
| 5,387,425 A | * | 2/1995 | Hsu et al. | 426/329 |
| 5,536,935 A | * | 7/1996 | Klotzsch et al. | 250/223 B |
| 5,542,004 A | * | 7/1996 | Constant et al. | 382/141 |
| 5,843,336 A | * | 12/1998 | Steelman | 516/117 |
| 6,226,081 B1 | * | 5/2001 | Fantone et al. | 356/239.6 |
| 6,316,034 B1 | * | 11/2001 | Daeschel et al. | 426/16 |

* cited by examiner

*Primary Examiner*—Hezron Williams
*Assistant Examiner*—Charles Garber
(74) *Attorney, Agent, or Firm*—Oblon, Spivak, McClelland, Maier & Neustadt, P.C.

(57) ABSTRACT

A method for evaluating the period of beer foam stability of sample of equal foam layer thicknesses comprising the steps of obtaining a sample by pouring a fixed amount of prescribed beer into a standard glass from a pouring height calculated to approximate a standard preset thickness, measuring the foam layer thickness and the period of foam stability of the sample, comparing the measured values with the standard foam layer thickness value, adjusting the beer pouring height to approximate the standard foam thickness more closely, pouring the fixed amount of the prescribed beer into a standard glass to obtain another sample, and measuring and storing the foam thickness value and period of foam stability of the sample, and reading the period of foam stability value corresponding to the standard foam layer thickness from a graph obtained by plotting the foam layer thickness data against the period of foam stability data for a plurality of samples obtained by repeating the above steps a number of times.

1 Claim, 9 Drawing Sheets

Fig. 8

| | Sample 1 | Sample 2 | Sample 3 |
|---|---|---|---|
| Velocity(0.1°/S) Tilt (0.1°) | 40  817<br>5  880 | 40  870<br>4  890 | 40  910<br>5  930 |
| Glass traverse | 10mm | 10mm | 15mm |
| Glass height | 115mm | 112mm | 110mm |

Acceleration 500 (0.1° PS/S)   End weight 140 (g)

METHOD AND APPARATUS FOR EVALUATING RETENTION TIME OF FOAM OF BEER

CROSS REFERENCE TO RELATED APPLICATIONS

This Application is a continuation of and claims the benefit of the earlier filing date of co-pending U.S. patent application Ser. No. 09/355,922, filed Aug. 10, 1999, which was also filed in JAPAN as Application No. 9/340198, filed on Dec. 10, 1997. The entire disclosure of the prior applications is considered as part of the disclosure of the accompanying application and is hereby incorporated by reference herein.

TECHNICAL FIELD

The present invention relates to a beer pouring method and apparatus, and more particularly to a beer pouring method and apparatus for pouring beer by movements similar to a person pouring beer into a vessel such as a glass in order to determine the period of the beer foam stability and a system for measuring and evaluating the period of the foam stability.

BACKGROUND ART

The inventors have developed an apparatus for pouring beer into a vessel which approximates the movements of a person pouring beer based on the concept that it is important to use the foam formed when beer is poured in a manner similar to a person manually pouring beer. An example of a head maintaining test is Japanese Patent Laid-Open No. 67342/1996.

In the apparatus, a beer bottle is secured and is pivoted about the mouth thereof at a fixed speed to a predetermined angle until the bottom of the bottle comes to a predetermined height (the distance to the bottom of the glass into which beer is poured from the mouth of the beer bottle). Thereafter, a predetermined amount of beer is poured into the glass and the period of the beer foam stability is evaluated from the time when the layer of foam is formed (the time until the foam disappears: hereinafter referred to as "period of foam stability"). In this method, a fixed amount of beer is poured. However, the fixed amount itself is not an essential requirement.

What is required is to make the foaming conditions equal. One factor relating to foaming when beer is poured into a glass is the pouring force and the time required for pouring when the same glass is used. For the evaluation of the foam stability property, it is necessary to control this factor to the same conditions. Controlling this factor to the same conditions means pouring a predetermined amount of beer in an equal amount of time. Accordingly, the object of evaluation of the foam stability is achieved by controlling the pouring time and the pouring amount to be equal.

The pouring amount is also related to the size of the pouring vessel and is set to an amount which does not cause the beer to overflow from the vessel including the foam and is not too small but the amount which makes the foaming conditions to be equal.

However, with the method described above, especially for bottles, bottles do not have the same shape, and an equal amount of beer may not be poured when bottles are tilted at the same angle. In other words, the foaming conditions may not be equal between beer bottles.

Further, in the pouring method described above, even though beer is poured under the same conditions for foam forming and foam stability, the shape and temperature of the pouring vessel, the state of the inner surface of the vessel and the pouring height (the amount of foam formed differs according to the force of impact of the beer striking the vessel, the amount of foam increasing as the force of impact increases), may be different and the layer of foam is frequently different.

DISCLOSURE OF THE INVENTION

According to the results of the research conducted by the inventors, foaming is different between different kinds of beer (good or bad foaming qualities), and a thicker layer of foam is formed by beer having better foaming qualities if the other conditions are identical. Further, since foaming and foam stability are different properties, it is not reasonable to determine the foam stability property from the period of the foam stability alone (the time until the ratio of the foam to the total amount of beer becomes smaller than a fixed value).

Accordingly, it is difficult to form a foam layer of an equal thickness on a sample, which is the essential requirement in an evaluation method.

Therefore, it is an object of the present invention to solve the above problem by making it possible to evaluate the beer foam stability property from the period of the foam stability on which a foam layer of equal thickness is formed by providing a method and apparatus for pouring beer as well as a system for measuring and evaluating the period of foam stability to realize measuring operation of the period of the foam stability.

To achieve this object, the present invention provides a method for evaluating period of beer foam stability, comprising the steps of pouring a fixed amount of prescribed beer into a standard glass from a height considered suitable for forming a layer of foam with the thickness of a predetermined standard to obtain a sample, measuring the foam thickness and period of foam stability of said sample, comparing the foam thickness value and period of foam stability value of said sample with said predetermined standard, for adjusting the pouring height to a height suitable for forming a foam thickness which approximates more closely the foam thickness of said preset standard and repeating the pouring of a fixed amount of prescribed beer into a standard glass to obtain a new sample, and for measuring and storing the foam thickness and period of foam stability of the newly obtained sample, repeating the above steps for a plurality of samples, reading the period of foam stability which corresponds to said preset standard from a graph obtained by plotting the foam layer thickness values of said plurality of samples versus the period of foam stability values.

The present invention further provides a method and an apparatus for tilting a beer bottle to pour beer into a glass, characterized in that the mouth of a bottle is positioned at a height for forming a foam layer of a thickness which approximates a preset standard, and a fixed amount of beer is poured into a glass placed below the mouth of the bottle by tilting the bottle.

The present invention offers an advantage is that the use of a novel beer pouring apparatus which can pour a fixed amount of beer makes it possible to evaluate the period of beer foam stability precisely from the thickness of the layer of foam formed on the beer.

BRIEF DESCRIPTION OF THE DRAWINGS

FIG. 8 is a view illustrating operation settings for obtaining a plurality of samples.

BEST MODE FOR CARRYING OUT THE INVENTION

Figure 1:
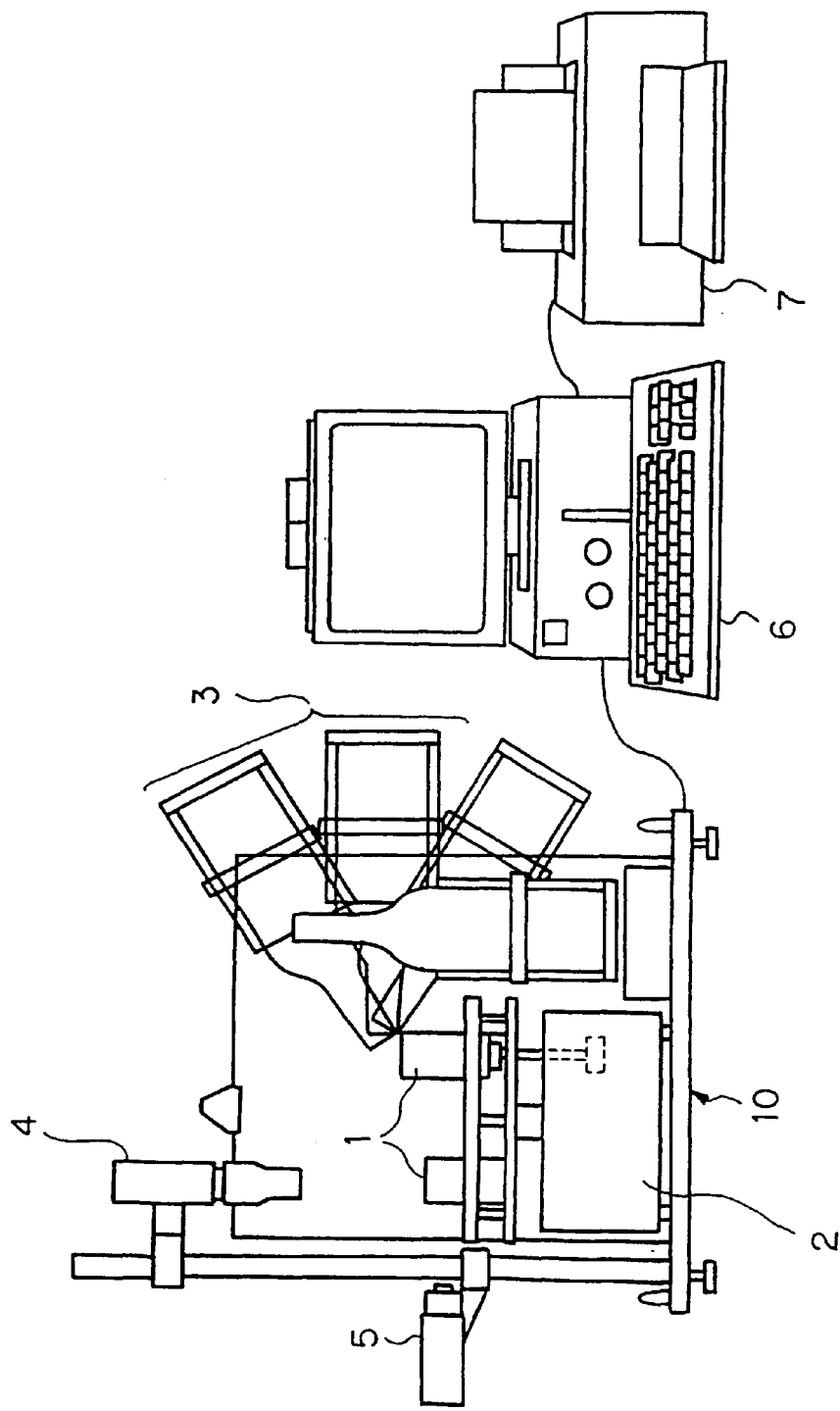
FIG. 1 is a schematic view showing a configuration of an apparatus for evaluating period of beer foam stability according to an embodiment of the present invention.

FIG. 1 is a schematic view showing a configuration of apparatus for evaluating a period of beer foam stability according to an embodiment of the present invention.

As shown in FIG. 1, a beer pouring apparatus 10 comprises a turntable driver 2 for supporting and moving the position of test glass 1 vertically and horizontally and between a beer pouring position and a foam observation position, a beer pouring mechanism 3 for holding and manipulating a beer bottle such that the beer bottle is pivoted at the mouth to raise the bottom to a tilted position for pouring beer into test glass 1 similar to movements of a person pouring beer and its drive, video camera 4 for observing the foam of the beer formed in test glass 1 from a vertical direction, and video camera 5 for measuring the thickness of the layer of foam from a horizontal direction.

Reference numeral 6 denotes a personal computer with a monitor for setting up and controlling operation of the beer pouring out apparatus and processing various data acquired, and 7 a printer for printing out measurement data. The apparatus for evaluating the period of the beer foam stability of the present embodiment is composed principally of personal computer 6 with a monitor, printer 7 and beer pouring apparatus 10.

Figure 2:
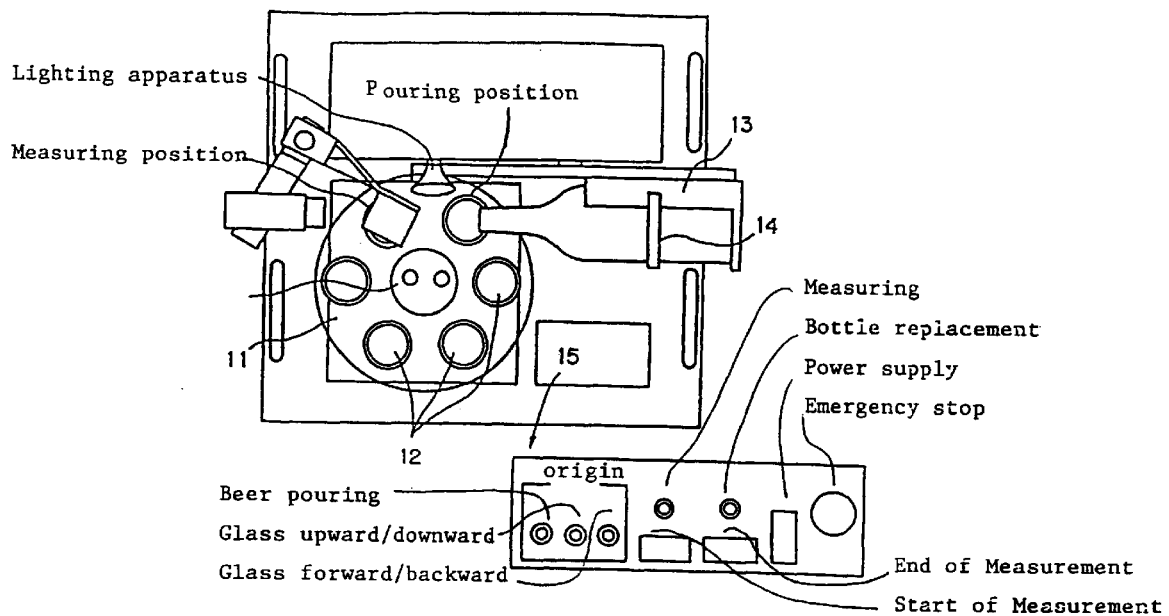
FIG. 2 is a top plan view (A) and a front elevational view (B) showing a configuration of a turntable driver.
Figure 2:
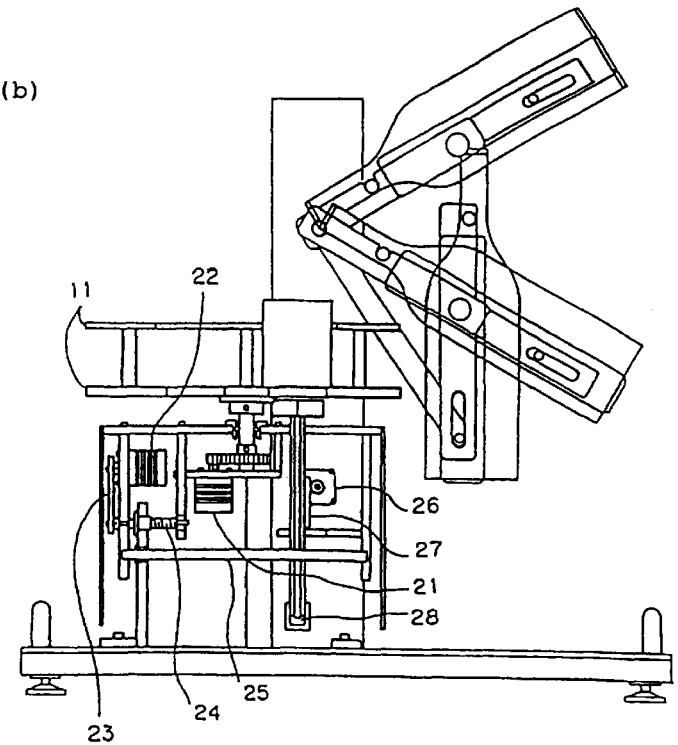

FIG. 2 is schematic views showing the construction of the turntable driver.

Referring to of FIG. 2(A), six small tables 12 for supporting test glasses are placed the same circle on turntable 11. As turntable 11 rotates, small tables 12 are successively fed to a measuring position after a fixed amount of beer is poured into each of them from a pouring position. The beer bottle is placed on a receiving portion of attachment 13 and fixedly supported by resilient fixing belt 14.

Referring to FIG. 2(B), turntable 11 is rotatably driven by rotary motor 21 and a reduction gear. The position of turntable 11 is adjustable in forward and backward directions (in leftward and rightward directions in of FIG. 2(B) along a linear shaft 25 by means of a forward/backward motor 22, a timing belt 23 and a ball screw 24. Each of the six small tables 12 is moved upwardly and downwardly at the pouring position by upward/downward motor 26 and rack and pinion gear 27 to adjust the distance between the glass and the spout. Load sensor 28 is provided at a lower end of the rack for detecting the weight of the glass in which beer is accommodated.

The beer pouring apparatus further includes an operating panel 15 as shown in of FIG. 2(A) and means for displaying basic operations and movements such as power-on of apparatus 10.

Figure 3:
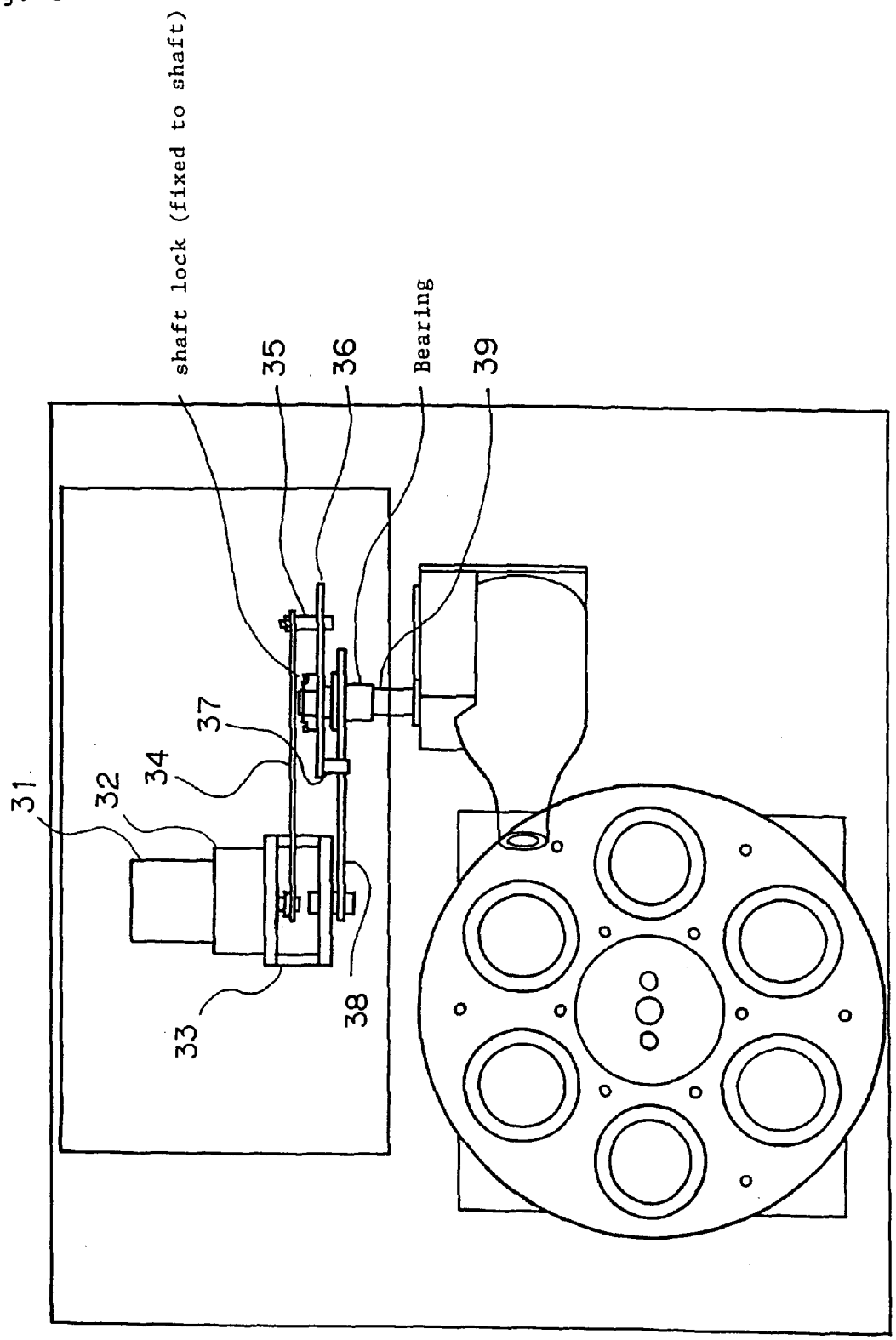
FIG. 3 is a schematic view showing a construction of a beer pouring mechanism and a driver therefor.

FIG. 3 is a schematic view showing a construction of the beer pouring mechanism and the driver.

Rotation of palse motor 31 is transmitted to the rotary shaft of a gear box 32. Casing 33 is attached to gear box 32. Lifting lever 34 is attached to the end of the rotation shaft extending from the gear box into case 33 and turned by it. The other end of lifting lever 34 is connected to the end of intermediate bar 36 by lifting pin 35. The mid-portion of intermediate bar 36 is attached on shaft 39 for being turned and engaging pin 37 is attached at the other end. One end of main bar 38 is attached for turning coaxially with the rotary shaft of casing 33 and the other end is attached for turning on shaft 39. Main bar 38 has a recess into which engaging pin 37 of intermediate bar 36 engages. Main bar 38 is fixedly attached to the upper portion of attachment 13 to hold a beer bottle.

Operation of the beer pouring mechanism and its drive will be described in order.

Figure 4:
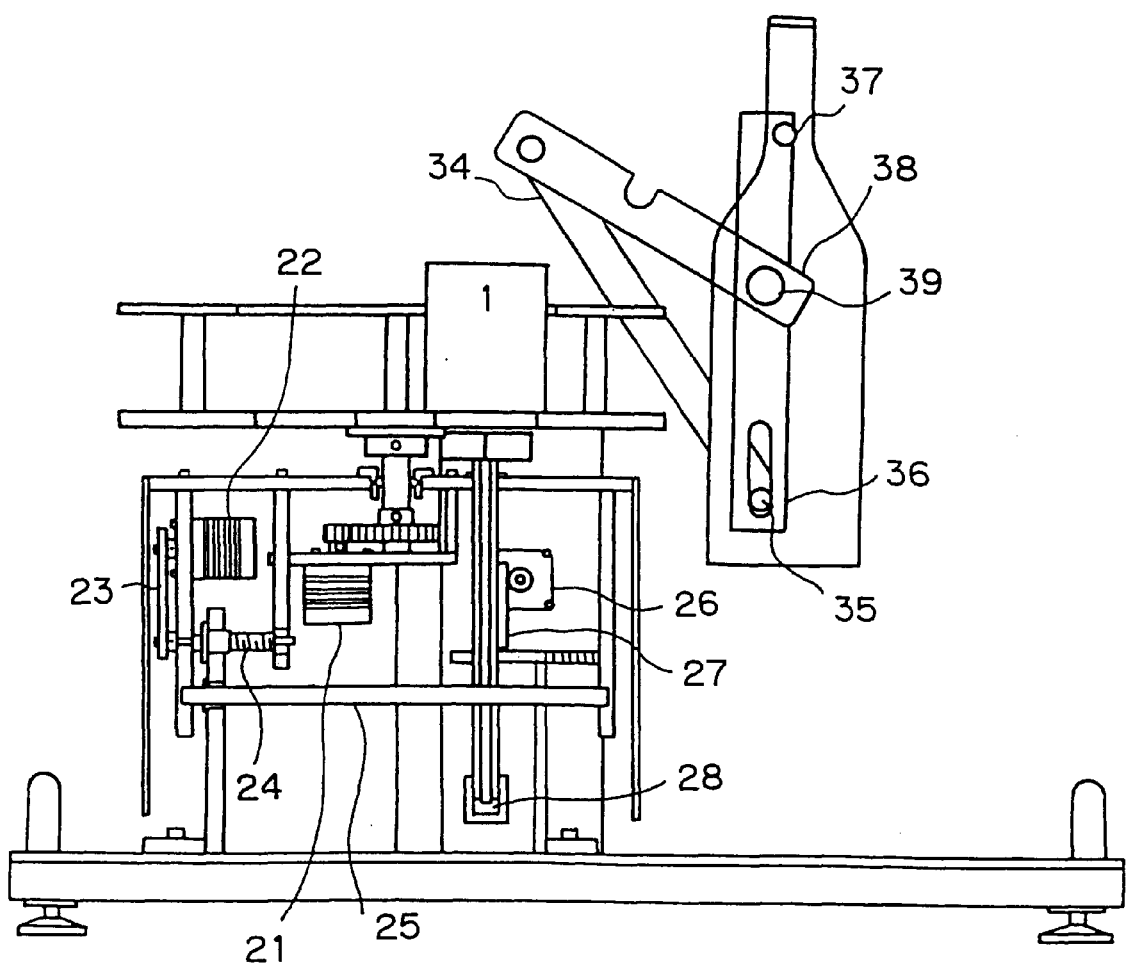
FIG. 4 is a view showing an operation state of the beer pouring mechanism.
Figure 5:
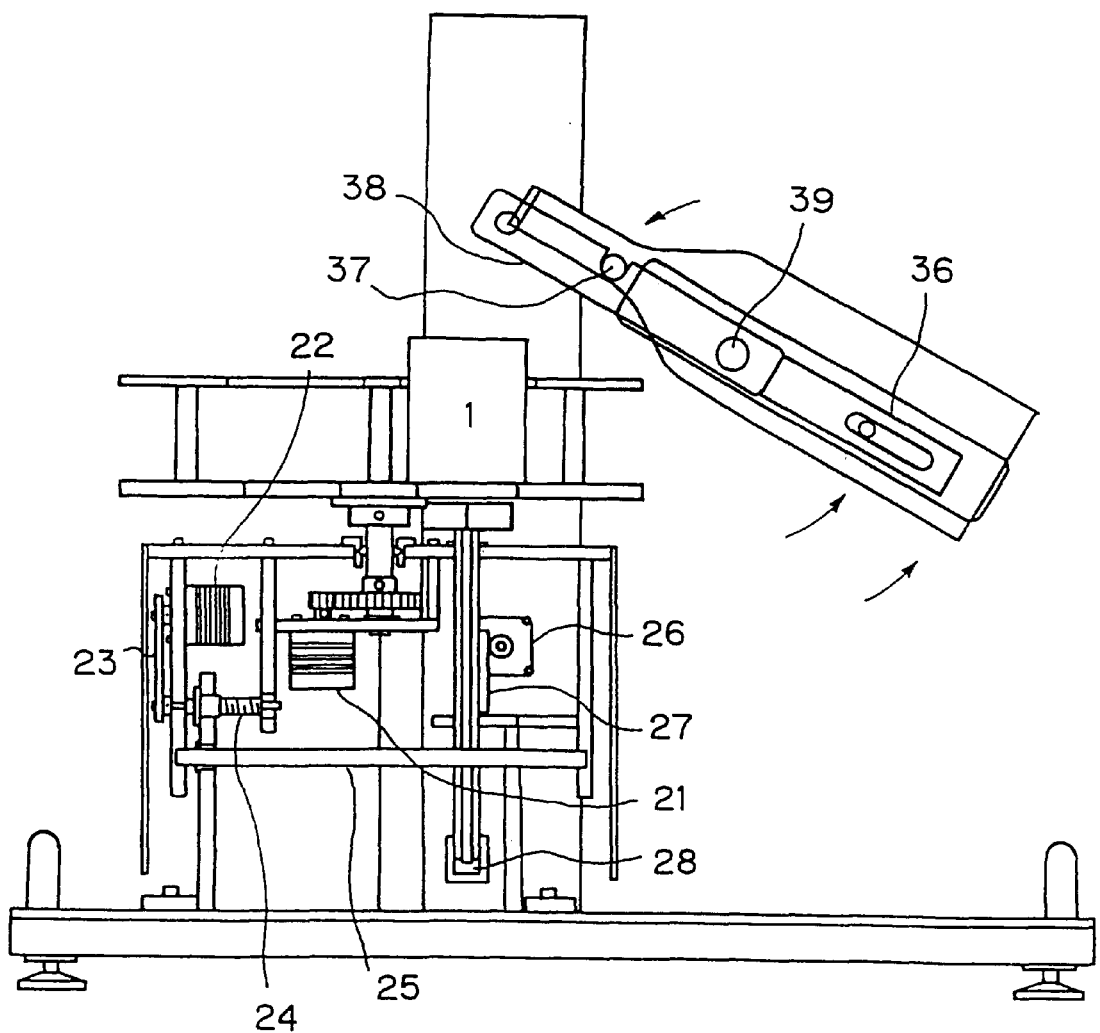
FIG. 5 is a view showing another operation state of the beer pouring mechanism.
Figure 6:
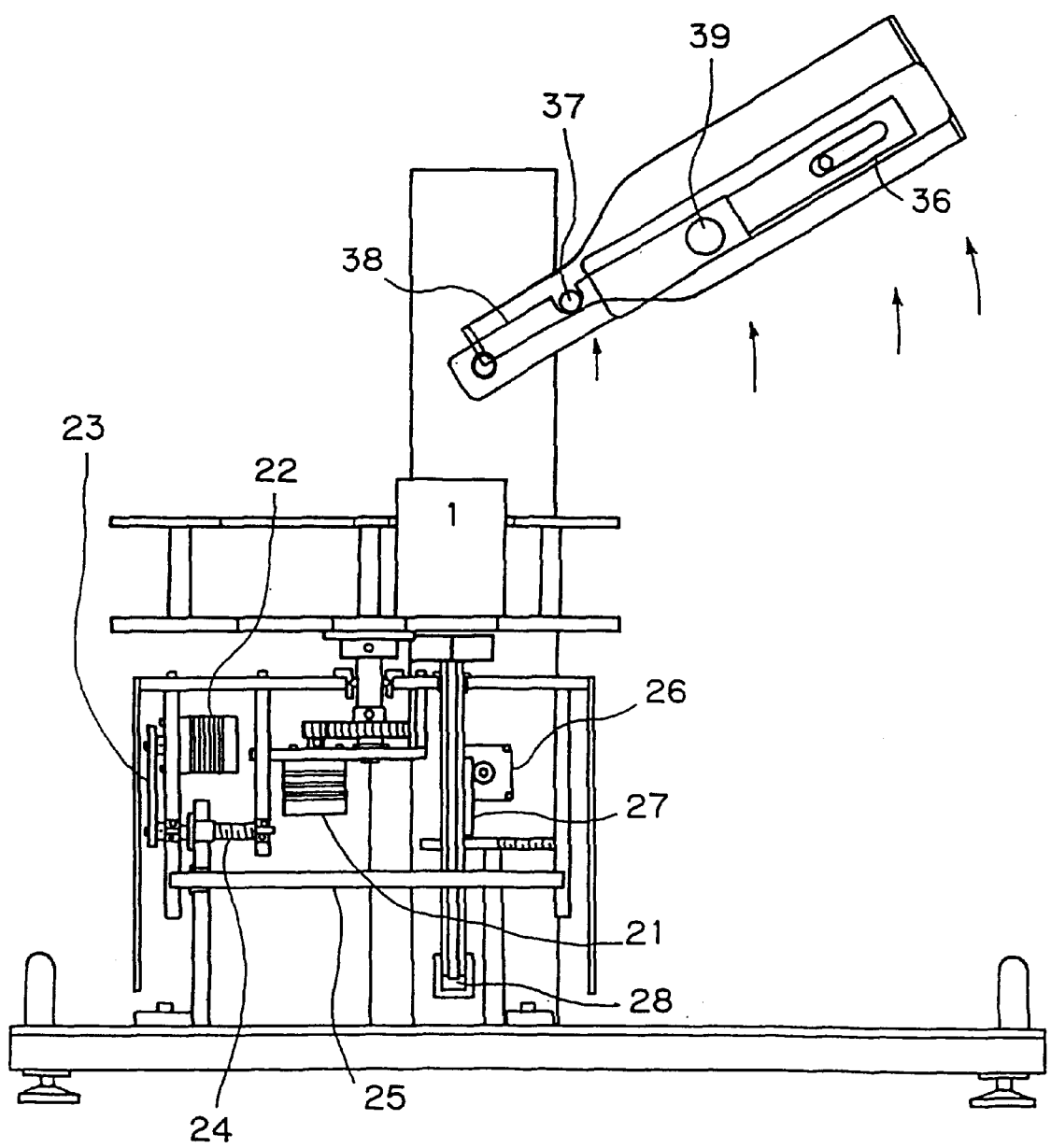
FIG. 6 is a view showing a further operation state of the beer pouring mechanism.

FIG. 4 shows a standby state before a test is performed with a beer bottle mounted on the beer pouring mechanism; FIG. 5 shows another state before beer begins to be poured; and FIG. 6 shows a still another state when pouring of a fixed amount of beer is completed. In FIGS. 4 to 6, the beer bottle holding mechanism (attachment, fixing belt and so forth) is not shown.

As described above, lifting lever 34 is pivoted about the rotary shaft of drive motor 31. Main bar 38 is supported on casing 33 coaxially with the rotary shaft of pulse motor 31, and intermediate bar 36 and main bar 38 are supported on shaft 39. Lifting lever 34 and intermediate bar 36 are connected by lifting pin 35, and intermediate bar 36 and main bar 38 are connectable by engaging pin 37.

As shown in FIG. 4, in the standby state before a test, the beer bottle and intermediate bar 36 are upright, and the three members of lifting lever 34, intermediate bar 36 and main bar 38 form a triangle.

When step motor 31 is driven to rotate, lifting lever 34 is pivoted about the rotary shaft of drive motor 31 accompanied by intermediate bar 36 through lifting pin 35, as shown in FIG. 5. Through the pivotal motion of, intermediate bar 36 and attachment 13, the bottom of the beer bottle is raised, and as the beer bottle is further tilted by its own weight until lifting lever 34 and intermediate bar 36 become aligned with each other, engaging pin 37 on the intermediate bar engages in the recess of intermediate bar 36. Consequently, the three members of lifting lever 34, intermediate bar 36 and main bar 38 are thereafter pivoted as a unit. The position of the mouth of the beer bottle is set near the center of the pivotal motion in a fixed position.

When the beer bottle is pivoted until the liquid level in the bottle becomes higher than the spout of the beer bottle, as shown in FIG. 6, pouring into the glass is initiated. The pouring into the glass continues as pulse motor 31 is driven to rotate to raise the bottom of the beer bottle. The weight of the glass into which beer is poured is detected by load sensor 28 provided below the small table, and the pouring is completed when load sensor 28 has detected a predetermined amount. Then, the bottle is returned to a position (tilt angle) at which beer is no longer poured. Then, the beer bottle stands by for quickly starting another pouring operation to obtain a new sample. If the beer bottle is returned to its original position the distance the beer is poured increases changing the foaming conditions. Therefore, the beer bottle is not returned to its original position. Production of a sample is thus completed.

Figure 7:
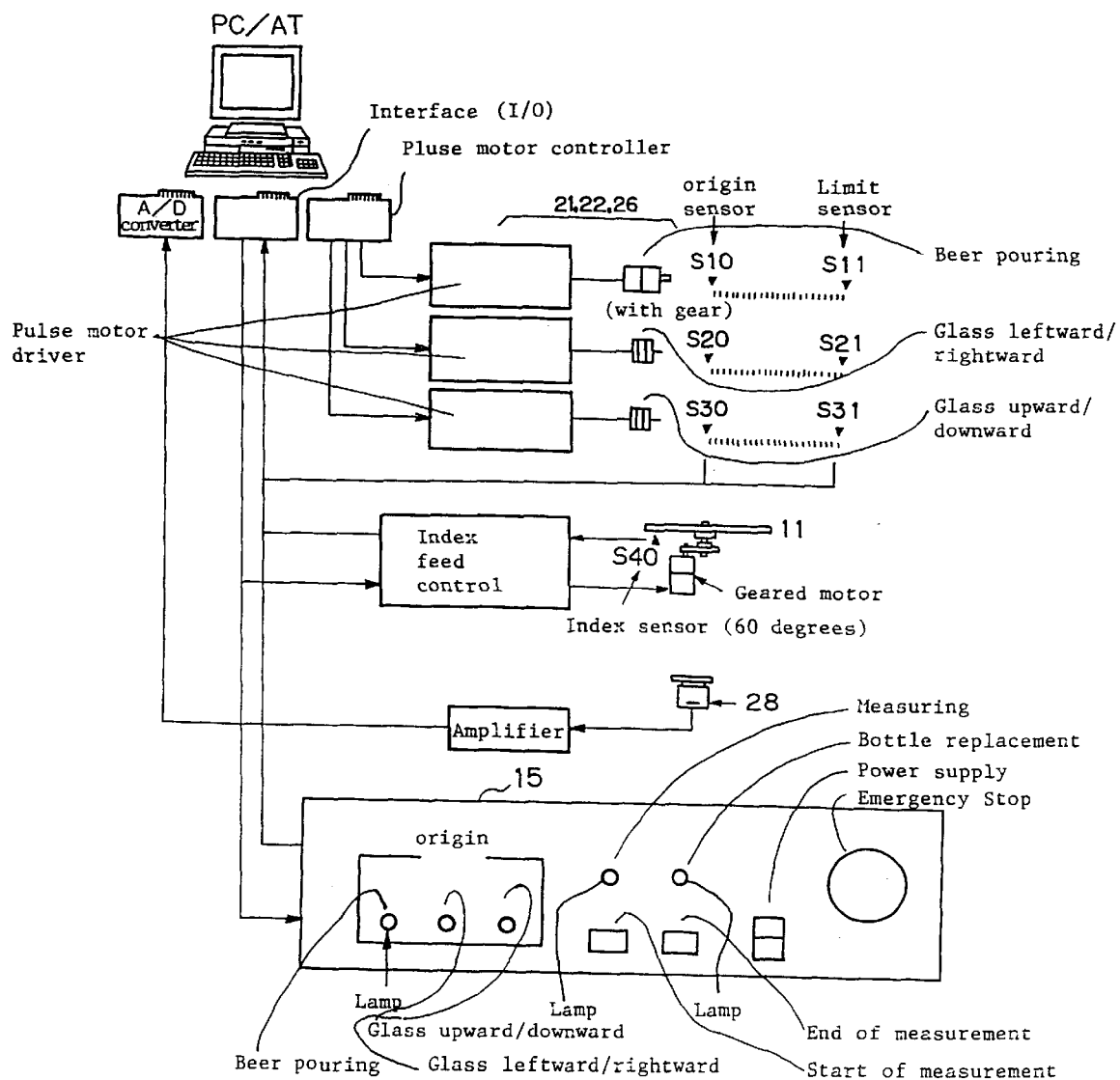
FIG. 7 is a block circuit diagram showing the electric connections of the apparatus for evaluating the period of beer foam stability.

FIG. 7 is a block circuit diagram showing electric connections in apparatus for evaluating the period of beer foam stability.

The driving system and the glass position adjusting mechanism in the beer pouring mechanism provide driving instructions from personal computer 6 to the pulse motors through a pulse motor controller. The turntable control mechanism exchanges information with the personal computer through an input/output interface and drives the turntable to rotate to successively move the test glasses to the pouring position and the measuring position. The positioning is performed by index sensors provided on the turntable side. In the present embodiment, since six test glasses are handled, a detector (limit sensor) is provided at each of positions angularly displaced by 60 degrees from the start position. Detectors (point of origin sensors) are provided at the start position such that the test glasses will be in position before an operator to obtain a sample begins.

Communication from load sensor 28 about the amount poured and exchange between operational panel 15 and the personal computer are performed through an A/D converter. Initialization of the beer pouring mechanism and the glass position adjusting mechanism and prevention of overrun is performed by transmitting detection information from the origin sensors and the limit sensors to the personal computer through an input/output interface.

Operation of the pouring apparatus is set up in advance by the personal computer. FIG. 8 shows an operation setting up display of the personal computer, and the velocity at which the beer bottle should be tilted (angular velocity [°/S]), the final weight (amount poured), and the glass is position horizontally (pouring position with respect to the diameter of the glass) and height of the glass (vertical position for pouring) can be set as desired for each sample.

The horizontal position of the glass can be adjusted by energizing forward/backward motor 22 to pour into the center of the glass or along the sides of the glass. The height of the glass can be adjusted by energizing upward/downward motor 26 in order to adjust the pouring height.

A method for evaluating period of beer foam stability will be described below.

In the present embodiment, the same kind of beer is used for a sample, and a standard layer thickness is set in advance (the ideal thickness of a foam layer when beer is poured is approximately 3 cm (irrespective of the shape and the size of the vessel)). A fixed amount of beer is poured from a height to approximate the standard foam thickness. The weight of the vessel in which the sample beer is poured is detected by load sensor 28, and when the fixed amount is reached, the pouring out is stopped. The sample obtained is transferred to the measuring process to measure the thickness of the foam and the time foamable. Data thus obtained are stored in a data processing unit (computer). The data processing unit therein determines the fixed foam layer thickness based on video information from video camera 5 (see FIG. 1) and determines the period of the foam stability from the time that elapses before the foam disappears based on video information of video camera 4.

When starting preparation of a second sample in succession from the same beer bottle, the foam layer thickness data obtained by the first measurement is compared with the aforementioned standard value, and glass 1 is moved upwardly or downwardly to adjust the beer pouring height for approximating the standard value. Then, preparation of a second sample is started.

The sequence of the foregoing operations is repeated a number of times, and the resulting data are processed by the computer and plotted on a foam layer thickness—foam life coordinate system. Then, a straight graph is drawn to proximate the plotted points on the coordinate system, and the period of the foam stability corresponding to the standard value is read from the graph. A value thus obtained is as the evaluation of the foam stability of the beer being evaluated.

The operation will be described in detail based on a particular example.

As a particular example, a glass having an effective height (9 cm) and an inner diameter (6 cm) was used, and approximately 150 g of beer was poured into the glass. The force at which the beer was poured was set so that 150 g of beer was poured in 5 to 6 seconds. The contents of this setting were stored in the personal computer and could be recalled arbitrarily. Thus, pouring operations of different pouring conditions can be set up in accordance with differences in types of beer, shape and size of the bottle (large bottle, middle bottle) and other conditions.

The standard value for comparing with a measured foam layer thickness was approximately 30 mm when considering the average value of data obtained by having a person pouring beer into a glass of the size described above.

Figure 9:
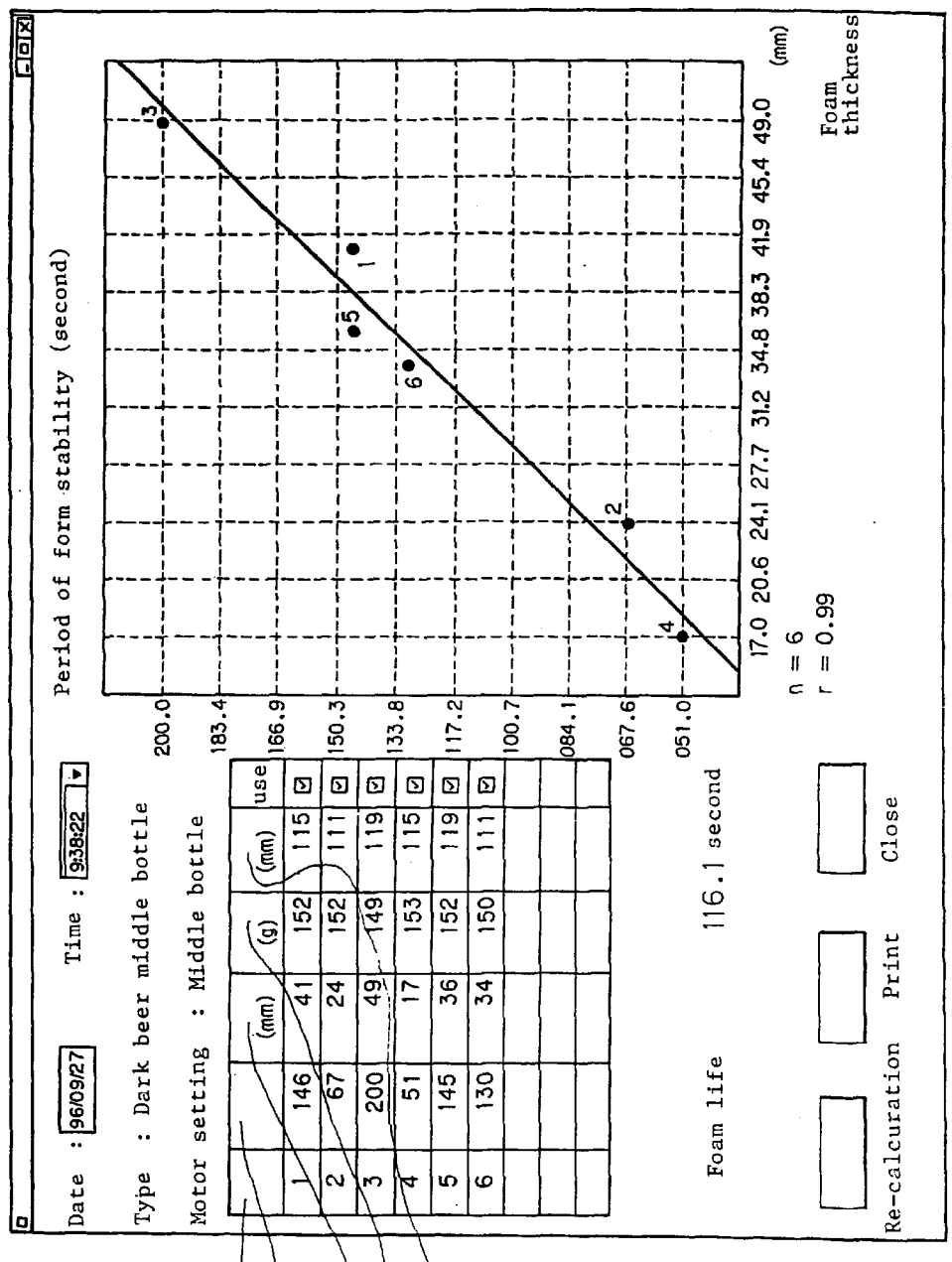
FIG. 9 is a view showing measurement data obtained from a plurality of samples and a graph of the foam thickness plotted against the period of foam stability.

FIG. 9 shows a display screen of the personal computer displaying results of measurement for six samples. Data obtained were plotted on a foam thickness (X-axis)—period of foam stability (Y-axis) coordinate system on the right-hand side of the screen, and the elementary graph most proximate to the distribution of the points was produced by the personal computer. Then, the period of the foam stability corresponding to the 30 mm standard foam thickness was read from the graph, and this value was considered the period of the beer foam stability used for the samples.

What is claimed is:

1. A method for evaluating a period of beer foam stability, said method comprising steps of:
   making a sample for measurement by pouring beer into a standard glass from a predetermined standard beer pouring height by pivoting a vessel that contains beer;
   imaging a side portion of the sample to measure a foam layer thickness based on the image of the side portion;
   imaging a surface of a foam layer of the sample to measure a period of foam stability until foam disappears based on the image of the surface of the foam layer;
   comparing the measured foam layer thickness with a predetermined standard foam layer thickness to calculate a compensating value based on a difference between the measured foam layer thickness and the predetermined standard foam layer thickness;
   making other samples for measurement by pouring beer to other standard glasses from a vessel whose beer pouring height is revised based on said compensating value;
   repeating the measuring steps of measuring a foam layer thickness and measuring a period of foam stability a predetermined number of times by using said other samples;
   plotting the measured data obtained in said repeating step to make a graph; and
   estimating the period of foam stability corresponding to the standard foam layer thickness based on the graph.

* * * * *